(12) United States Patent
Gill et al.

(10) Patent No.: US 11,452,533 B2
(45) Date of Patent: Sep. 27, 2022

(54) GUIDE WIRE TIP HAVING ROUGHENED SURFACE

(71) Applicant: Abbott Cardiovascular Systems Inc., Santa Clara, CA (US)

(72) Inventors: Puneet Kamal Singh Gill, Anaheim, CA (US); Jonathan Durcan, Temecula, CA (US); Jakub Truty, La Verne, CA (US); Matthew J. Chludzinski, Poway, CA (US); John Simpson, Carlsbad, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 654 days.

(21) Appl. No.: 16/245,032

(22) Filed: Jan. 10, 2019

(65) Prior Publication Data
US 2020/0222067 A1    Jul. 16, 2020

(51) Int. Cl.
*A61B 17/22* (2006.01)
*A61M 25/09* (2006.01)
*A61B 17/00* (2006.01)

(52) U.S. Cl.
CPC .... *A61B 17/22* (2013.01); *A61B 2017/00858* (2013.01); *A61B 2017/22038* (2013.01); *A61B 2017/22094* (2013.01); *A61M 2025/09083* (2013.01); *A61M 2025/09108* (2013.01); *A61M 2025/09133* (2013.01); *A61M 2025/09175* (2013.01)

(58) Field of Classification Search
CPC .......... A61B 17/22; A61B 2017/22038; A61B 2017/22042; A61B 2017/22044; A61B 2017/22094; A61M 2025/09083; A61M 2025/09108; A61M 2025/09133; A61M 2025/09175; A61M 2025/09183
See application file for complete search history.

(56) References Cited

U.S. PATENT DOCUMENTS

| | | | |
|---|---|---|---|
| 1,878,671 | A | 9/1932 | Cantor |
| 2,022,065 | A | 11/1935 | Wappler |
| 2,047,535 | A | 7/1936 | Wappler |
| 3,196,876 | A | 7/1965 | Miller |
| 3,452,742 | A | 7/1969 | Muller |
| 3,516,412 | A | 6/1970 | Bernard |
| 3,687,142 | A | 8/1972 | Leibinzohn |

(Continued)

FOREIGN PATENT DOCUMENTS

| | | |
|---|---|---|
| DE | 19728337 A1 | 1/1999 |
| EP | 377453 A1 | 7/1990 |

(Continued)

OTHER PUBLICATIONS

International Search Report, dated Apr. 14, 2020, 2 pages, from counterpart application No. PCT/US20/12793.

*Primary Examiner* — Devin B Henson
(74) *Attorney, Agent, or Firm* — Fulwider Patton LLP

(57) ABSTRACT

A guidewire for use in penetrating through complex and stenosed lesions. The distal tip of the guidewire has a roughened surface to increase frictional engagement with calcified and fibrous tissue to increase the penetration of the distal tip and the guidewire into and through the lesion and reduce the likelihood of deflection of the guidewire tip. The average surface roughness of the distal tip is in the range from 1 micron to 200 microns.

16 Claims, 8 Drawing Sheets

(56) References Cited

U.S. PATENT DOCUMENTS

| | | |
|---|---|---|
| 3,731,671 A | 5/1973 | Mageoh |
| 3,789,841 A | 2/1974 | Antoshkiw |
| 3,802,440 A | 4/1974 | Ziegler et al. |
| 3,841,308 A | 10/1974 | Tate |
| 3,867,945 A | 2/1975 | Long |
| 3,924,632 A | 12/1975 | Cook |
| 3,928,519 A | 12/1975 | Kashiyama et al. |
| 3,941,119 A | 3/1976 | Corrales |
| 3,973,556 A | 8/1976 | Fleischhacker et al. |
| 3,999,551 A | 12/1976 | Spitz et al. |
| 4,003,369 A | 1/1977 | Heilman et al. |
| 4,013,079 A | 3/1977 | Lindemann et al. |
| 4,020,829 A | 5/1977 | Willson et al. |
| 4,080,706 A | 3/1978 | Heilman et al. |
| 4,085,757 A | 4/1978 | Pevsner |
| 4,169,464 A | 10/1979 | Obrez |
| 4,195,637 A | 4/1980 | Gleichner et al. |
| 4,204,528 A | 5/1980 | Termanini |
| 4,211,741 A | 7/1980 | Ostoich |
| 4,257,421 A | 3/1981 | Beal |
| 4,283,447 A | 8/1981 | Flynn |
| 4,306,566 A | 12/1981 | Sinko |
| 4,345,602 A | 8/1982 | Yoshimura et al. |
| 4,385,635 A | 5/1983 | Ruiz |
| 4,388,076 A | 6/1983 | Waters |
| 4,419,095 A | 12/1983 | Nebergall et al. |
| 4,425,919 A | 1/1984 | Alston et al. |
| 4,456,017 A | 6/1984 | Miles |
| 4,464,176 A | 8/1984 | Wijayarathna |
| 4,504,268 A | 3/1985 | Herlitze |
| 4,531,943 A | 7/1985 | Van Tassel et al. |
| 4,534,363 A | 8/1985 | Gold |
| 4,538,622 A | 9/1985 | Samson et al. |
| 4,545,390 A | 10/1985 | Leary |
| 4,554,929 A | 11/1985 | Samson et al. |
| 4,563,181 A | 1/1986 | Wijayarathna et al. |
| 4,619,274 A | 10/1986 | Morrison |
| 4,643,194 A | 2/1987 | Fogarty |
| 4,665,906 A | 5/1987 | Jervis |
| 4,682,607 A | 7/1987 | Vaillancourt et al. |
| 4,690,175 A | 9/1987 | Ouchi et al. |
| 4,721,117 A | 1/1988 | Mar et al. |
| 4,739,768 A | 4/1988 | Engelson |
| 4,748,986 A | 6/1988 | Morrison et al. |
| 4,757,827 A | 7/1988 | Buchbinder et al. |
| 4,763,647 A | 8/1988 | Gambale |
| 4,779,628 A | 10/1988 | Machek |
| 4,798,598 A | 1/1989 | Bonello et al. |
| 4,811,743 A | 3/1989 | Stevens |
| 4,813,434 A | 3/1989 | Buchbinder et al. |
| 4,815,478 A | 3/1989 | Buchbinder et al. |
| 4,832,047 A | 5/1989 | Sepetka et al. |
| 4,841,976 A | 6/1989 | Packard et al. |
| 4,846,186 A | 7/1989 | Box et al. |
| 4,867,174 A | 9/1989 | Skribiski |
| 4,873,983 A | 10/1989 | Winters |
| 4,884,579 A | 12/1989 | Engelson |
| 4,895,168 A | 1/1990 | Machek |
| 4,917,102 A | 4/1990 | Miller et al. |
| 4,917,104 A | 4/1990 | Rebell |
| 4,922,924 A | 5/1990 | Gambale et al. |
| 4,925,445 A | 5/1990 | Sakamoto et al. |
| 4,932,419 A | 6/1990 | de Toledo |
| 4,934,380 A | 6/1990 | de Toledo |
| 4,955,384 A | 9/1990 | Taylor et al. |
| 4,955,862 A | 9/1990 | Sepetka |
| 4,991,602 A | 2/1991 | Amplatz et al. |
| 4,992,924 A | 2/1991 | Gousset et al. |
| 5,003,990 A | 4/1991 | Osypka |
| 5,061,273 A | 10/1991 | Yock |
| 5,061,395 A | 10/1991 | Meng |
| 5,063,935 A | 11/1991 | Gambale |
| 5,065,769 A | 11/1991 | de Toledo |
| 5,069,217 A | 12/1991 | Fleischhacker |
| 5,069,226 A | 12/1991 | Yamauchi et al. |
| 5,084,022 A | 1/1992 | Claude |
| 5,084,151 A | 1/1992 | Vallana et al. |
| 5,095,915 A | 3/1992 | Engelson |
| 5,111,829 A | 5/1992 | Alvarez de Toledo |
| 5,120,308 A | 6/1992 | Hess |
| 5,127,917 A | 7/1992 | Niederhauser et al. |
| 5,129,890 A | 7/1992 | Bates et al. |
| 5,135,503 A | 8/1992 | Abrams |
| 5,144,959 A | 9/1992 | Gambale et al. |
| 5,147,317 A | 9/1992 | Shank et al. |
| 5,171,383 A | 12/1992 | Sagae et al. |
| 5,174,302 A | 12/1992 | Palmer |
| 5,176,149 A | 1/1993 | Grenouillet |
| 5,178,158 A | 1/1993 | de Toledo |
| 5,184,627 A | 2/1993 | de Toledo |
| 5,209,730 A | 5/1993 | Sullivan |
| 5,213,111 A | 5/1993 | Cook et al. |
| 5,217,026 A | 6/1993 | Stoy et al. |
| 5,226,423 A | 7/1993 | Tenerz et al. |
| 5,228,453 A | 7/1993 | Sepetka |
| 5,229,211 A | 7/1993 | Murayama et al. |
| 5,230,348 A | 7/1993 | Ishibe et al. |
| 5,238,004 A | 8/1993 | Sahatjian et al. |
| 5,241,970 A | 9/1993 | Johlin, Jr. et al. |
| 5,246,009 A | 9/1993 | Adams |
| 5,253,653 A | 10/1993 | Daigle et al. |
| 5,259,353 A | 11/1993 | Nakai et al. |
| 5,259,393 A | 11/1993 | Corso et al. |
| 5,267,574 A | 12/1993 | Viera et al. |
| 5,303,714 A | 4/1994 | Abele et al. |
| 5,313,967 A | 5/1994 | Lieber et al. |
| 5,333,620 A | 8/1994 | Moutafis et al. |
| 5,341,818 A | 8/1994 | Abrams et al. |
| 5,345,945 A | 9/1994 | Hodgson et al. |
| 5,358,493 A | 10/1994 | Schweich et al. |
| 5,368,048 A | 11/1994 | Stoy et al. |
| 5,372,144 A | 12/1994 | Mortier et al. |
| 5,379,779 A | 1/1995 | Rowland et al. |
| 5,380,307 A | 1/1995 | Chee et al. |
| 5,385,152 A | 1/1995 | Abele et al. |
| 5,402,799 A | 4/1995 | Colon et al. |
| 5,404,887 A | 4/1995 | Prather |
| 5,406,960 A | 4/1995 | Corso |
| 5,421,955 A | 6/1995 | Lau et al. |
| 5,433,200 A | 7/1995 | Fleischhacker |
| 5,437,288 A | 8/1995 | Schwartz et al. |
| 5,443,455 A | 8/1995 | Hergenrother et al. |
| 5,452,726 A | 9/1995 | Burmeister et al. |
| 5,460,187 A | 10/1995 | Daigle et al. |
| 5,465,732 A | 11/1995 | Abele |
| 5,465,733 A | 11/1995 | Hinohara et al. |
| 5,479,938 A | 1/1996 | Weier |
| 5,497,783 A | 3/1996 | Urick et al. |
| 5,497,785 A | 3/1996 | Viera |
| 5,497,786 A | 3/1996 | Urick |
| 5,498,250 A | 3/1996 | Prather |
| 5,516,336 A | 5/1996 | McInnes et al. |
| 5,573,520 A | 11/1996 | Schwartz et al. |
| 5,606,979 A | 3/1997 | Hodgson |
| 5,606,981 A | 3/1997 | Tartacower et al. |
| 5,622,184 A | 4/1997 | Ashby et al. |
| 5,636,641 A | 6/1997 | Fariabi |
| 5,640,970 A | 6/1997 | Arenas |
| 5,666,969 A | 9/1997 | Urick et al. |
| 5,702,419 A | 12/1997 | Berry et al. |
| 5,706,826 A | 1/1998 | Schwager |
| 5,722,424 A | 3/1998 | Engelson |
| 5,746,701 A | 5/1998 | Noone |
| 5,749,837 A | 5/1998 | Palermo et al. |
| 5,750,206 A | 5/1998 | Hergenrother et al. |
| 5,772,424 A | 6/1998 | Nokelainen |
| 5,772,609 A | 6/1998 | Nguyen et al. |
| 5,797,857 A | 8/1998 | Obitsu |
| 5,807,279 A | 9/1998 | Viera |
| 5,827,201 A | 10/1998 | Samson et al. |
| 5,830,155 A | 11/1998 | Frechette et al. |
| 5,836,892 A | 11/1998 | Lorenzo |
| 5,836,893 A | 11/1998 | Urick |
| 5,840,046 A | 11/1998 | Deem |

(56) References Cited

U.S. PATENT DOCUMENTS

| | | | |
|---|---|---|---|
| 5,865,767 A | 2/1999 | Frechette et al. | |
| 5,876,356 A | 3/1999 | Viera et al. | |
| 5,885,227 A | 3/1999 | Finlayson | |
| 5,891,055 A | 4/1999 | Sauter | |
| 5,984,877 A | 11/1999 | Fleischhacker | |
| 5,984,878 A | 11/1999 | Engelson | |
| 6,059,738 A | 5/2000 | Stoltze et al. | |
| 6,270,524 B1 | 8/2001 | Kim | |
| 6,340,441 B1 | 1/2002 | Meyer et al. | |
| 6,390,993 B1 | 5/2002 | Cornish et al. | |
| 6,409,754 B1 | 6/2002 | Smith et al. | |
| 6,666,829 B2 | 12/2003 | Cornish et al. | |
| 6,673,025 B1 | 1/2004 | Richardson et al. | |
| 6,884,225 B2 | 4/2005 | Kato et al. | |
| 7,955,512 B2 | 6/2011 | Park et al. | |
| 7,972,283 B2 | 7/2011 | Cornish et al. | |
| 8,500,657 B2 | 8/2013 | Brown | |
| 9,173,983 B2 | 11/2015 | Charlebois et al. | |
| 2009/0270890 A1* | 10/2009 | Robinson | A61B 34/76 606/159 |
| 2016/0183967 A1* | 6/2016 | McGuckin, Jr. | A61B 17/320758 606/159 |
| 2018/0193606 A1 | 7/2018 | Patel et al. | |
| 2020/0164183 A1* | 5/2020 | Koike | A61M 25/09 |

FOREIGN PATENT DOCUMENTS

| | | | |
|---|---|---|---|
| EP | 407965 A1 | 1/1991 | |
| EP | 744186 A1 | 11/1996 | |
| EP | 763365 A1 | 3/1997 | |

\* cited by examiner

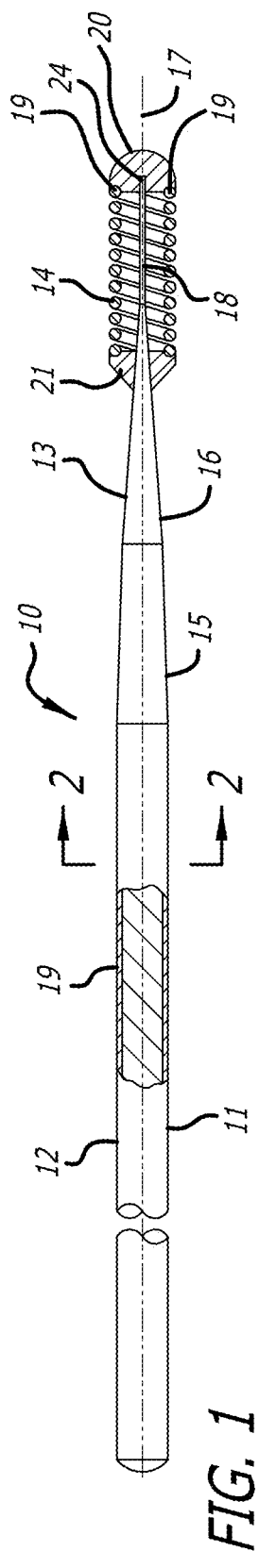
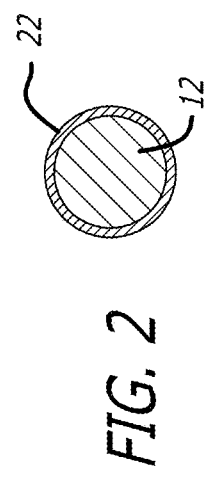
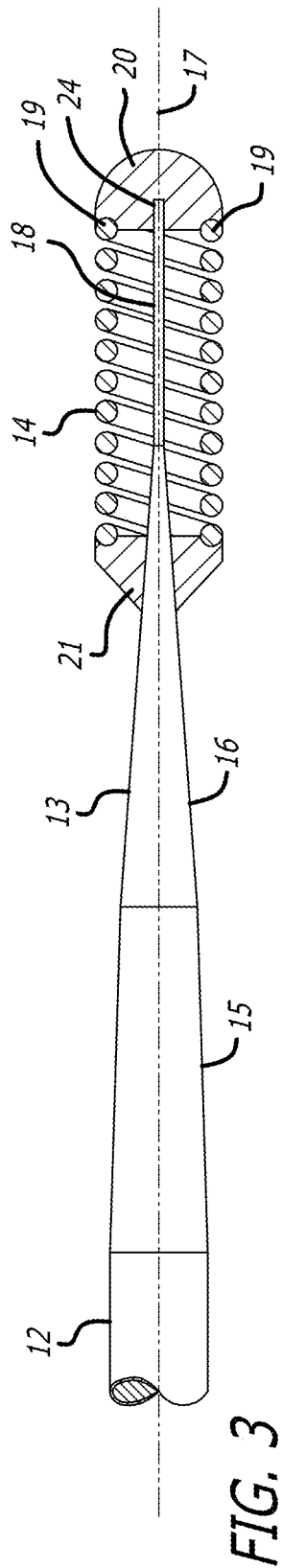
FIG. 1
FIG. 2
FIG. 3

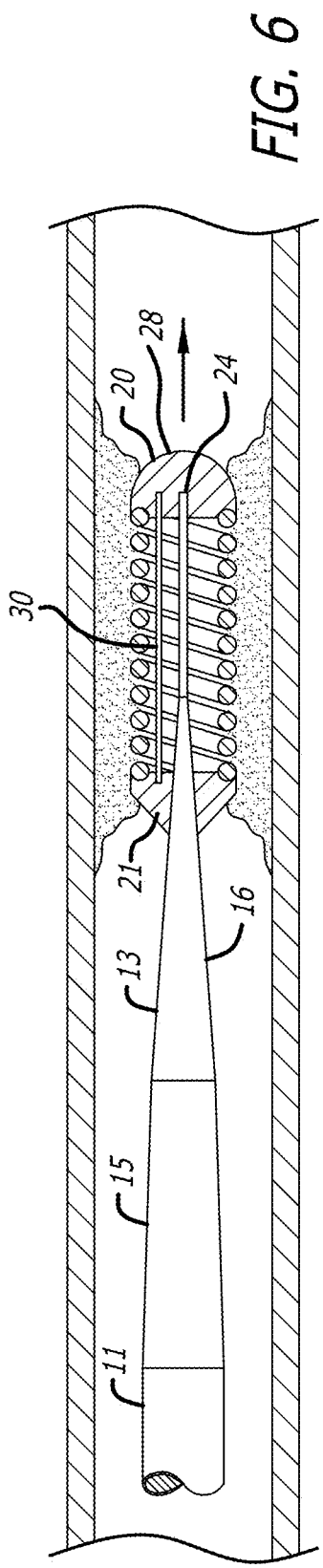
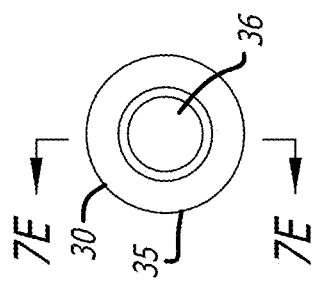
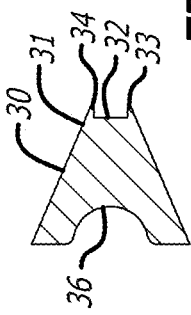

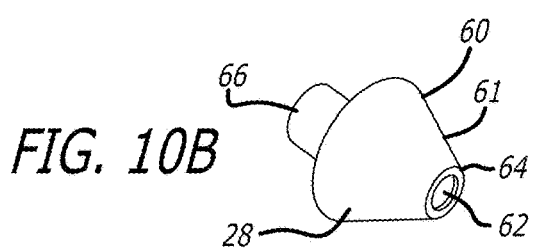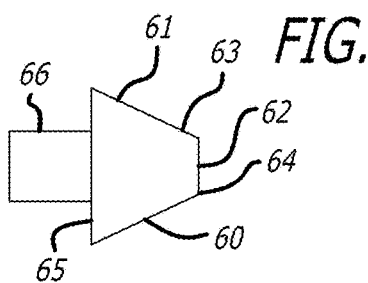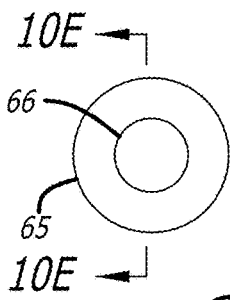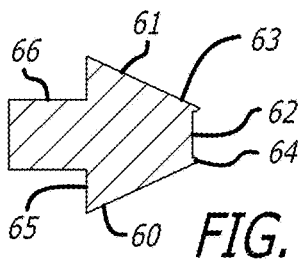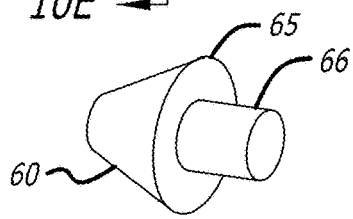
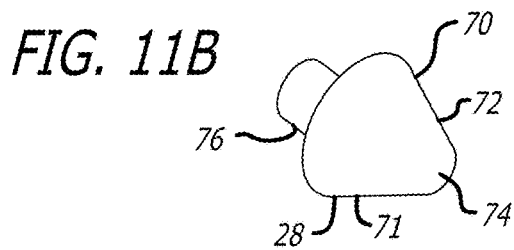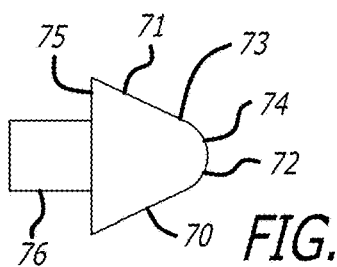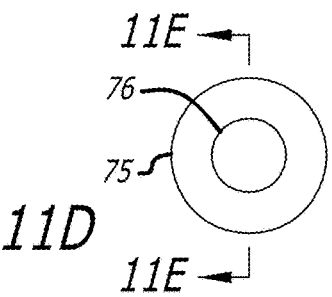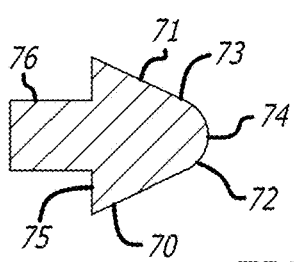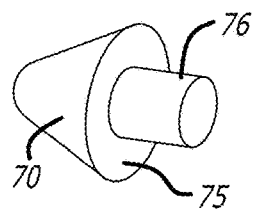

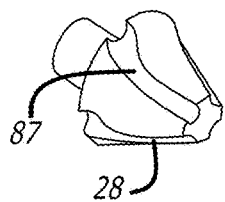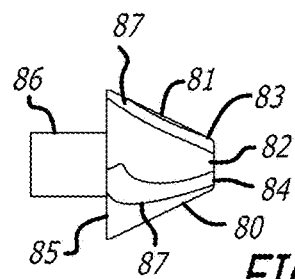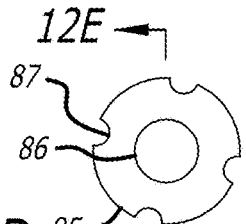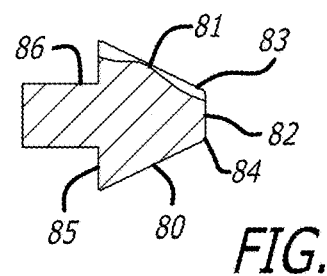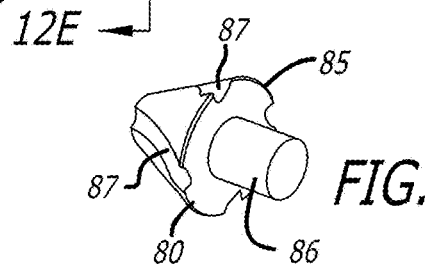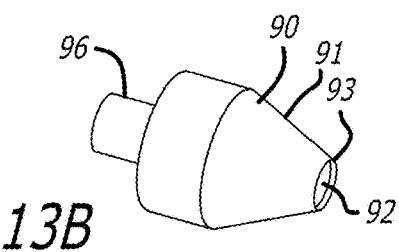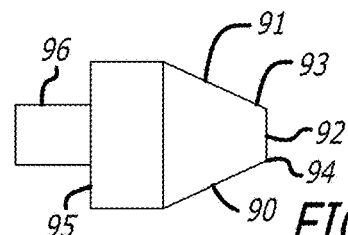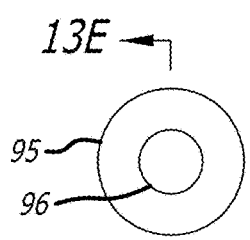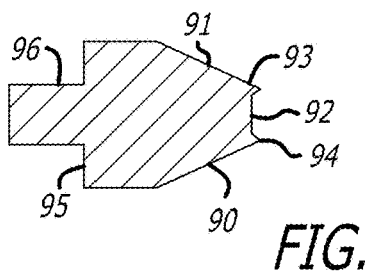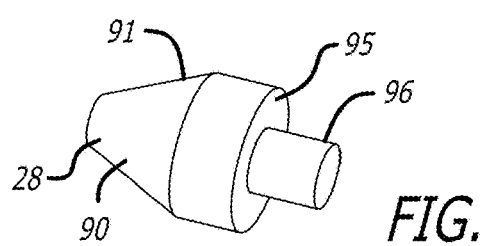

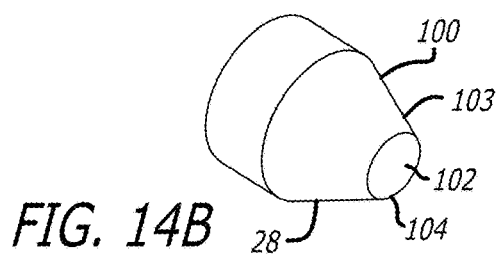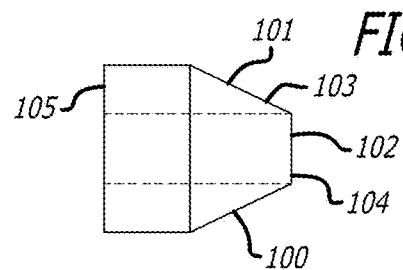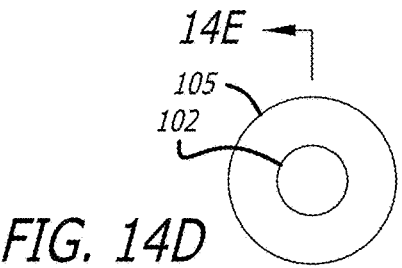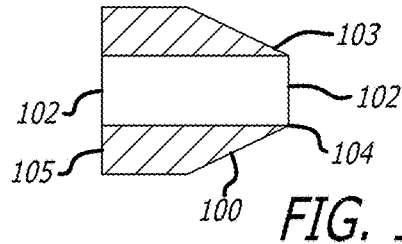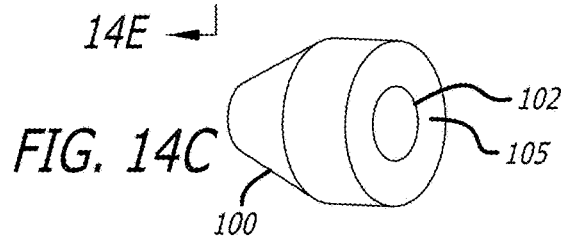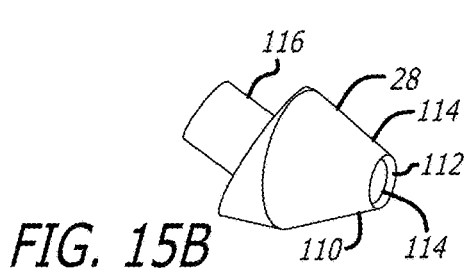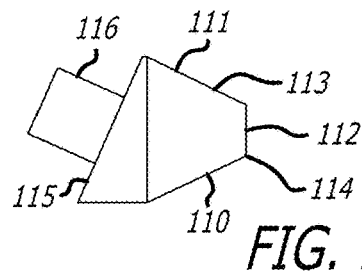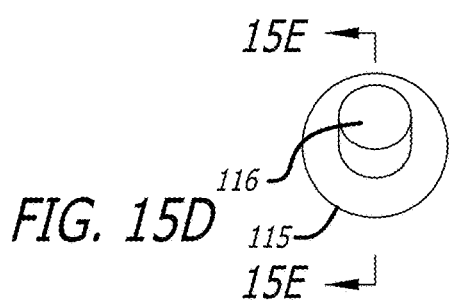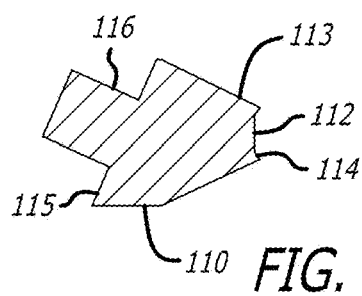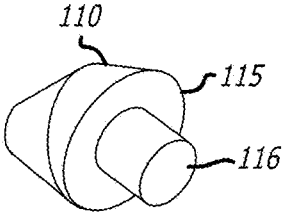

GUIDE WIRE TIP HAVING ROUGHENED SURFACE

BACKGROUND

The present invention generally relates to guidewires, and in particular, the accurate positioning and delivery of a guidewire for passing through a chronic total occlusion ("CTO") of a body vessel.

A CTO is a severe narrowing of a blood vessel, such as a coronary artery, that results in a complete or nearly complete occlusion of the primary vessel. CTOs are quite common in diseased coronary arteries and typically occur where plaque is formed in the artery, gradually reducing the size of the lumen in the artery until it becomes quite small and results in thrombus formation resulting in a stenosis forming a total occlusion. As the total occlusion becomes chronic, the stenosis or blockage generally has a tendency to continue to grow with fibrous end caps being formed at the proximal and distal ends of the occlusion. These fibrous end caps tend to be fairly tough but do have varying degrees of toughness.

Angioplasty and stent implantation procedures are commonly employed to treat CTOs or other stenoses that form within the vascular anatomy of a patient. During an angioplasty, or percutaneous transluminal coronary angioplasty ("PTCA") procedure, a guiding catheter is advanced through the vasculature of the patient to a desired point. A guidewire, positioned within a balloon catheter, is extended from a distal end of the guiding catheter into the patient's coronary artery until it penetrates and crosses a blockage to be dilated. The balloon catheter is then advanced through the guiding catheter and over the previously introduced guidewire, until it is properly positioned across the blockage. Once properly positioned, the balloon is inflated to a predetermined size such that the material causing the blockage is compressed against the arterial wall, thereby expanding the passageway of the artery. The balloon is subsequently deflated, blood flow resumes through the dilated artery, and the balloon catheter is removed. Typically, a stent is implanted to maintain vessel patency.

In attempting to treat such chronic occlusions, there is a need to have guidewires which can extend through the stenoses forming the chronic occlusions so that various types of treatments can be performed. Heretofore attempts to place guidewires across such stenoses or blockages have resulted in the guidewires following fissures in the plaque and creating false lumens or with the guidewire being directed in such a manner so as to perforate the wall of the vessel causing a vessel dissection. In attempting to perform such a guidewire crossing, it often has been necessary to exchange the guidewire for a stiffer wire, which is time consuming.

In light of the above discussion, a need exists in the art for a guidewire tip designed to penetrate through complex and stenosed lesions and configured for use with multiple guidewires employed in treating intravascular blockages. Any solution to the above need should increase the likelihood of a successful crossing of a CTO. Moreover, any proposed solution should be adaptable for use with a variety of guidewire types and configurations.

SUMMARY OF THE INVENTION

The present invention is directed to an improved guidewire providing enhanced distal support while having a flexible distal tip to provide acceptable steerability and little risk of damage to vessel or chamber linings when advanced through a patient's body lumen such as veins and arteries.

The guidewire of the present invention has an elongated core member with proximal and distal core sections and a flexible tubular body such as a helical coil disposed about and secured to the distal section of the core member.

The flexible tubular body such as a helical coil is secured by its distal end to the distal end of the distal core section in a conventional fashion. The helical coil may be secured by its distal end by soldering, brazing, gluing or welding to form a rounded distal tip to the guiding member as done with commercially available guidewires for procedures within a patient's coronary artery. In one embodiment, the soldered distal tip is roughened so that the outer surface of the distal tip has an average surface roughness no greater than 200 microns. The roughened distal tip engages the stenosed lesion (CTO) and has increased friction which ensures that the roughened distal tip more easily penetrates the stenosed lesion rather than deflecting off of it. In one embodiment, the roughened distal tip has an average surface roughness in the range from 1 micron to 10 microns. In another embodiment, the roughened distal tip has an average surface roughness in the range from 20 microns and 150 microns. In another embodiment, the roughened distal tip has an average surface roughness in the range from 1 micron to 200 microns.

These and other advantages of the invention will become more apparent from the following detailed description of the invention when taken in conjunction with the accompanying exemplary drawings.

BRIEF DESCRIPTION OF THE DRAWINGS

FIG. 1 is an elevational view partially in section of a guidewire embodying features of the invention.

FIG. 2 is a transverse cross-sectional view of the guidewire shown in FIG. 1 taken along lines 2-2.

FIG. 3 is an enlarged elevational view partially in section of the distal portion of the guidewire shown in FIG. 1 depicting the tapers of the distal core section.

FIG. 6 is an elevational view of the distal end of the guidewire advancing distally in a vessel and the roughened distal tip penetrating through a stenosed lesion.

FIG. 7A is a side view of a conically-shaped distal tip.

FIG. 7B is a front perspective view of the conically-shaped distal tip depicting a recessed portion.

FIG. 7C is a rear perspective view of the conically-shaped distal tip.

FIG. 7D is a rear view of the conically-shaped distal tip depicting a cavity.

FIG. 7E is a cross-sectional view taken along lines 7E-7E of the distal tip depicting the recessed portion and the cavity.

FIG. 10A is a side view of one embodiment of the distal tip depicting a frusto-conical-shaped section and a stem extending therefrom.

FIG. 10B is a front perspective view of the embodiment of FIG. 10A depicting a recessed portion.

FIG. 10C is a rear perspective view of the embodiment of FIG. 7A depicting the stem portion.

FIG. 10D is a rear view of the embodiment of FIG. 10A depicting the stem portion.

FIG. 10E is a cross-sectional view taken along lines 10E-10E of the distal tip depicted in FIG. 7A showing the recessed portion and the stem portion.

FIG. 11A is a side view of a mushroom-shaped distal tip.

FIG. 11B is a front perspective view of the mushroom-shaped distal tip.

FIG. 11C is a rear perspective view of the mushroom-shaped distal tip depicting a stem portion.

FIG. 11D is a rear view of the mushroom-shaped distal tip depicting the stem portion.

FIG. 11E is a cross-sectional view taken along lines 11E-11E of the mushroom-shaped distal tip depicting the stem portion.

FIG. 12A is a side view of a frusto-conical-shaped distal tip having a stem portion and having arcuate grooves.

FIG. 12B is a front perspective view of the embodiment shown in FIG. 12A.

FIG. 12C is a rear perspective view of the embodiment depicted in FIG. 12A showing the stem portion.

FIG. 12D is a rear view of the embodiment of FIG. 12A depicting the stem portion and the arcuate grooves.

FIG. 12E is a cross-sectional view taken along lines 12E-12E of the embodiment of FIG. 12A depicting the stem portion and the arcuate grooves.

FIG. 13A is a side view of another embodiment of the distal tip.

FIG. 13B is a front perspective view of the embodiment of FIG. 13A depicting a recessed portion.

FIG. 13C is a rear perspective view of the embodiment of FIG. 13A depicting a stem portion.

FIG. 13D is a rear view of the embodiment of the FIG. 13A depicting the stem portion.

FIG. 13E is a cross-sectional view of taken along lines 13E-13E of the embodiment of FIG. 13A depicting the recessed portion and the stem portion.

FIG. 14A is a side view of another embodiment of the distal tip.

FIG. 14B is a front perspective view of the embodiment of FIG. 14A depicting a through-hole.

FIG. 14C is a rear perspective view of the embodiment of FIG. 14A depicting the through-hole.

FIG. 14D is a rear view of the embodiment of FIG. 14A depicting the through-hole.

FIG. 14E is a cross-sectional view taken along lines 14E-14E of the embodiment of FIG. 14A depicting the through-hole.

FIG. 15A is a side view of an angulated distal tip.

FIG. 15B is a front perspective view of the angulated distal tip having a recessed portion and a stem portion.

FIG. 15C is a rear perspective view of the angulated distal tip depicting the stem portion.

FIG. 15D is a rear view of the angulated distal tip depicting the stem portion.

FIG. 15E is a cross-sectional view taken along lines 15E-15E of the angulated distal tip depicting the recessed portion and the stem portion.

DETAILED DESCRIPTION OF THE PREFERRED EMBODIMENTS

Figure 4:
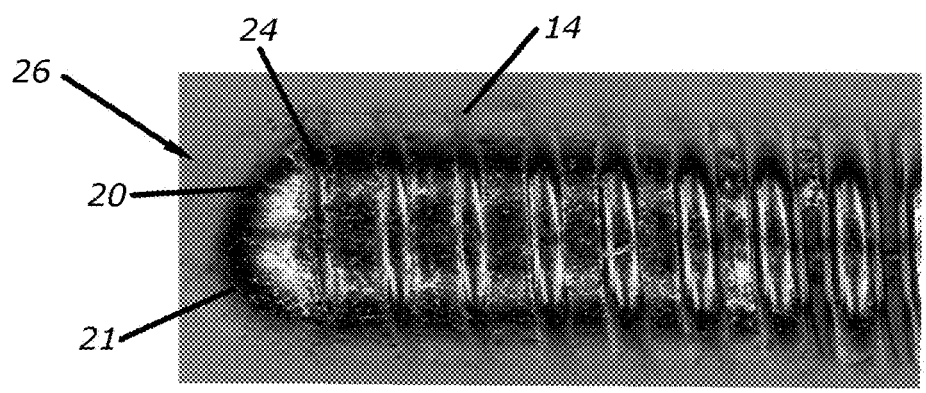
FIG. 4 is a micro-photograph of an elevational view of the distal end and distal tip of a guidewire depicting the rounded, half-dome shape of the distal tip before being modified.

FIGS. 1-3 depict a guidewire 10 which is a presently preferred embodiment thereof which has a core member 11 with a proximal core section 12, a distal core section 13 and a helical coil 14. The distal core section 12 has a first tapered segment 15 and a second tapered core segment 16 which is distally contiguous to the first tapered core segment. The second tapered segment 16 tapers at a greater degree than the first tapered segment and this additional taper provides a much smoother transition when the distal portion of the guidewire 10 is advanced through a tortuous passageway. The degree of taper of the first tapered core segment 15, i.e., the angle between the longitudinal axis 17 and a line tangent to the first tapered core segment 15 typically is about 2° to about 10°, whereas the taper of the second tapered core segment 16, i.e., the angle between the longitudinal axis and the second tapered core segment is larger than the first angle and typically is about 5° to about 10° such as is shown in the enlarged view of the guidewire 10 in FIG. 3. While only two tapered core segments are shown in the drawings, any number of tapered core segments can be employed. Moreover, all of a multiple of tapered core segments need not have increasing degrees of tapers in distal direction. However, two or more contiguous tapered core segments over a length of about 5 to 15 cm should have distally increasing degrees of tapering.

Typically, the first tapered segment is about 3 cm in length and the second tapered segment is about 4 cm in length. In a presently preferred embodiment, the guidewire 10 has a proximal core section 12 of about 0.014 inch (0.36 mm) in diameter, the first tapered core segment has a diameter ranging from 0.014 inch down to about 0.008 inch (0.36-0.20 mm) and the second tapered core segment has a diameter ranging from about 0.008 inch to about 0.002 inch (0.20-0.05 mm). A flattened distal section 18 extends from the distal end of the second tapered core segment 16 to the distal tip 20, which secures the distal section 18 of the core member 11 to the distal end 19 of the helical coil 14. A body of solder 21 secures the proximal end of the helical coil 14 to an intermediate location on the second tapered segment 16.

The core member 11 is coated with a lubricious coating 22 such as a fluoropolymer, e.g., TEFLON® available from DuPont, which extends the length of the proximal core section 12. The distal section 13 is also provided a lubricous coating, not shown for purposes of clarity, such as a MICROGLIDE™ coating used by the present assignee, Abbott Cardiovascular Systems, Inc., on many of its commercially available guidewires. A hydrophilic coating may also be employed.

The core member may be formed of stainless steel, NiTi alloys or combinations thereof or other high strength alloys as is well known in the art.

The helical coil 14 is formed of a suitable radiopaque material such as platinum or alloys thereof or formed of other material such as stainless steel and coated with a radiopaque material such as gold. The wire from which the coil is made generally has a transverse diameter of about 0.003 inch (0.05 mm). The overall length of the helical coil 14 is typically about 3 cm. Multiple turns of the distal portion of coil 14 may be expanded to provide additional flexibility.

Figure 5A:
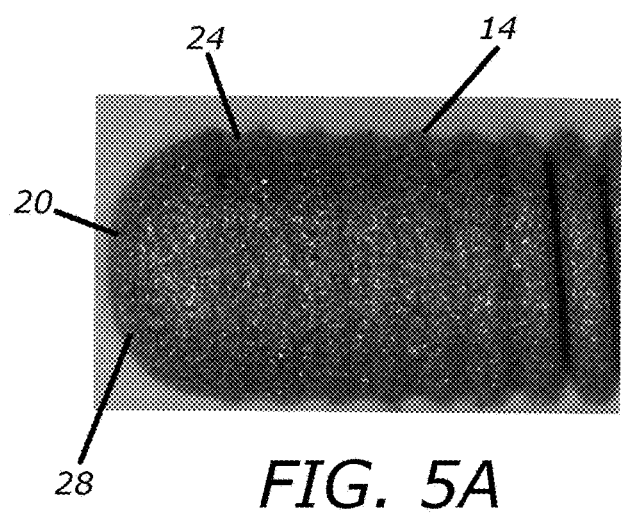
FIGS. 5A and 5B are micro-photographs of an elevational view of the roughened surface of the distal tip and wire coils of the guidewire of FIG. 4.
Figure 5B:
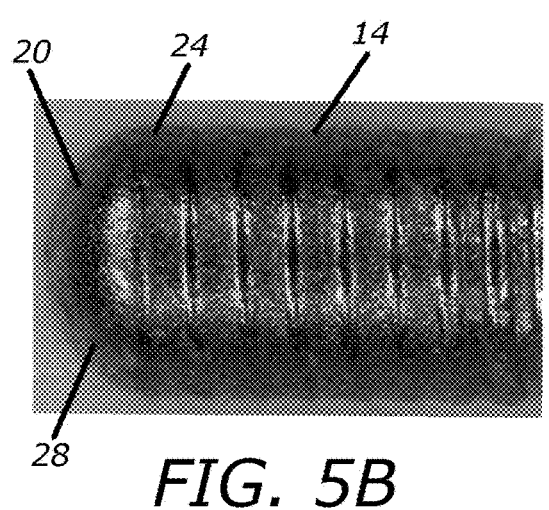
Figure 8B:
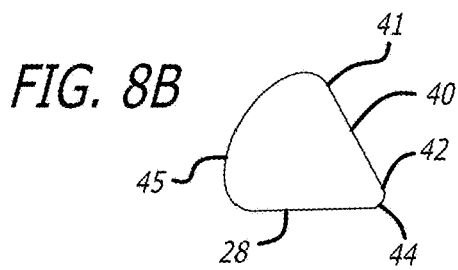
FIG. 8B is a front perspective view of the conically-shaped distal tip.
Figure 8A:
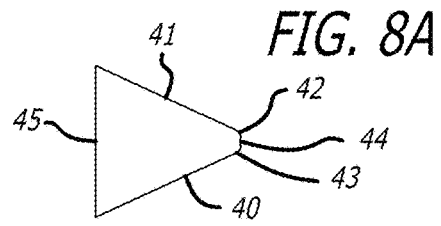
FIG. 8A is side view of a conically-shaped distal tip.
Figure 8D:
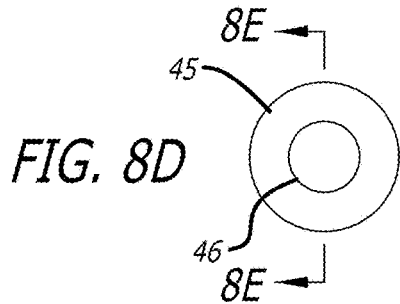
FIG. 8D is a rear view of the conically-shaped distal tip depicting the cavity.
Figure 8E:
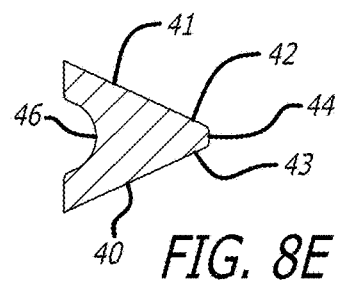
FIG. 8E is a cross-sectional view taken along lines 8E-8E of the distal tip depicting the cavity.
Figure 8C:
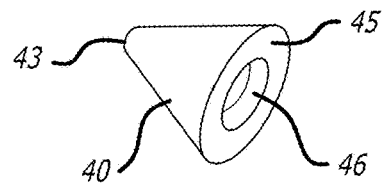
FIG. 8C is a rear perspective view of the conically-shaped distal tip depicting a cavity.
Figure 9B:
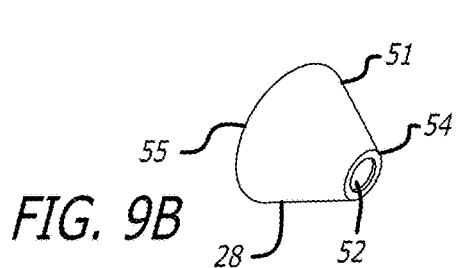
FIG. 9B is a front perspective view of the frusto-conical-shaped distal tip depicting a recessed portion.
Figure 9A:
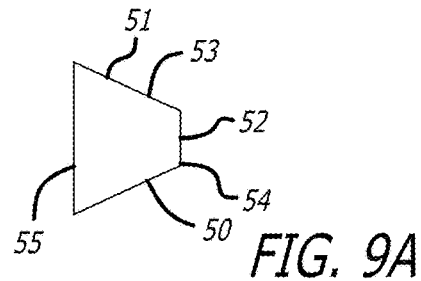
FIG. 9A is a side view of a frusto-conical-shaped distal tip.
Figure 9D:
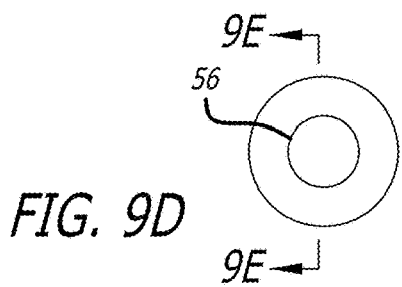
FIG. 9D is a rear view of the frusto-conical-shaped distal tip depicting the cavity.
Figure 9E:
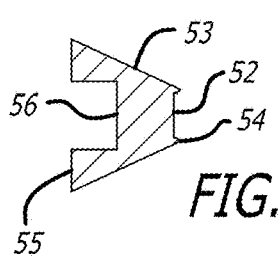
FIG. 9E is a cross-sectional view taken along lines 9E-9E of the distal tip depicting the recessed portion and the cavity.
Figure 9C:
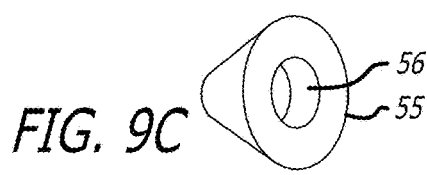
FIG. 9C is a rear perspective view of the frusto-conical-shaped distal tip depicting a cavity.
Figure 16A:
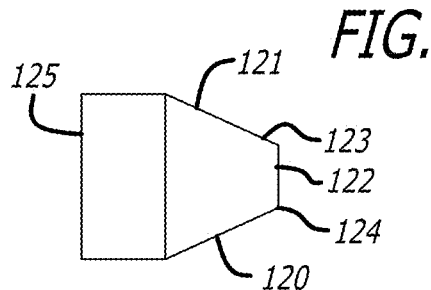
FIG. 16A is a side view of another embodiment of the distal tip.
Figure 16B:
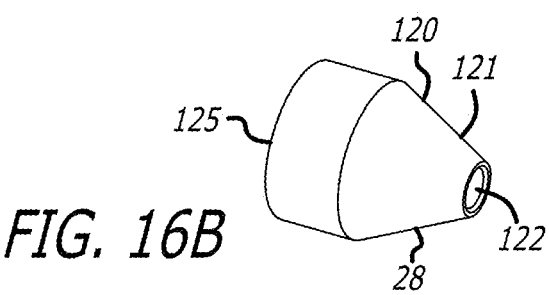
FIG. 16B is a front perspective view of the embodiment of FIG. 16A depicting a recessed portion.
Figure 16C:
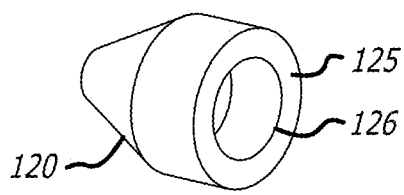
FIG. 16C is a rear perspective view of the embodiment of FIG. 16A depicting a cavity.
Figure 16D:
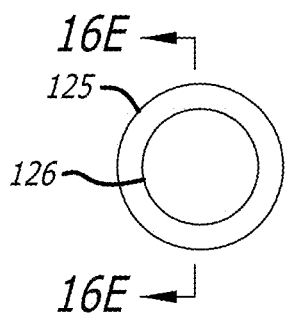
FIG. 16D is a rear view of the embodiment of FIG. 16A depicting the cavity.
Figure 16E:
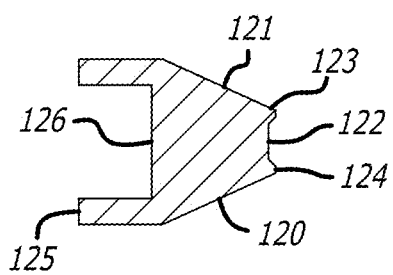
FIG. 16E is a cross-sectional view taken along lines 16E-16E of the embodiment of FIG. 16A depicting the recessed portion and the cavity.

In keeping with the invention and as shown in FIGS. 1-6, a guidewire 10 has an elongated core member 11 having a proximal core section 12 and a distal core section 13. The distal core section 13 has a distal end 24 which typically has a helical coil 14 mounted thereon. A distal tip 20 is mounted on the distal end 24 and is attached to the helical coil 14. In one embodiment, as shown in FIGS. 4-5B, the distal tip 20 is formed from a body of solder 21 and formed into a half-dome shape 26 on the distal end 24. Since the body of solder typically is smooth when formed, the distal tip 20 is treated to form a roughened surface 28. The roughened surface 28 is used to more easily penetrate calcified and fibrous tissue or lesions (chronic total occlusion CTO) by increasing the friction between the roughened surface 28 and the lesion. When the distal tip 20 is smooth as seen in FIG. 4, it has a tendency to slide off of the calcified lesion and fail to penetrate the lesion. The roughened surface 28 of FIGS. 5A and 5B will more easily penetrate the calcified lesion because the roughened surface sticks to the lesion and will not deflect or slide away, allowing the physician to advance the guidewire through the lesion. In the embodiment of FIG. 5A, the body of solder was micro bead blasted with aluminum oxide media while mounted on the distal end 24 to form the roughened surface 28. In the embodiment of FIG. 5B, the body of solder was micro bead blasted with sodium bicarbonate media while mounted on the distal end 24 to form the roughened surface 28. In one embodiment, the average surface roughness of the roughened surface 28 is in the range from 20 microns to 150 microns. In one embodiment, the average surface roughness of the roughened surface 28 is in the range from 1 micron to 200 microns. The micro bead blasting media is not limited to aluminum oxide and sodium bicarbonate, rather any suitable abrasive media can be used. The micro-blasting process disclosed herein is well known in the art and need not be further described.

In another embodiment as shown in FIGS. 1-4, 6 and 7A-16E, a guidewire 10 has an elongated core member 11 having a proximal core section 12 and a distal core section 13. The distal core section 13 has a distal end 24 which typically has a helical coil 14 mounted thereon. A distal tip 20 is mounted on the distal end 24 and is attached to the helical coil 14. In one embodiment, as shown in FIG. 4, the distal tip 20 is formed from a body of solder 21 and formed into a half-dome shape 26 on the distal end 24. Since the body of solder typically is smooth when formed, the distal tip 20 is treated to form a roughened surface 28. The roughened surface 28 is used to more easily penetrate calcified and fibrous tissue or lesions (chronic total occlusion CTO) by increasing the friction between the roughened surface 28 and the lesion. When the distal tip 20 is smooth as seen in FIG. 4, it has a tendency to slide off of the calcified lesion and fail to penetrate the lesion. The roughened surface 28 of FIGS. 6 and 7A-16E will more easily penetrate the calcified lesion because the roughened surface sticks to the lesion and will not deflect or slide away, allowing the physician to advance the guidewire through the lesion. In the embodiment of FIGS. 7A-16E, the body of solder was treated by laser roughening to form the roughened surface 28. In these embodiments, the average surface roughness of the laser roughened surface 28 is in the range of 1 micron to 10 microns. In one embodiment, the average surface roughness of the laser roughened surface 28 is in the range from 1 micron to 200 microns.

Other surface treatments are contemplated to impart the disclosed surface roughness 28 and include micro machining, sand paper, chemical etching, wire brush, chemical vapor deposition, or physical vapor deposition.

While the roughened surface 28 of the distal tip 20 shown in FIGS. 5A and 5B was formed by micro bead blasting while mounted on the distal end 24, it might be more preferable to form the distal tip 20 with a roughened surface 28 before mounting the distal tip 20 onto the distal end 24. As shown in FIGS. 7A-16E, different embodiments of the distal tip are shown having different structural characteristics and prior to being treated to form a roughened surface and prior to being mounted on the distal tip. The distal tips shown in FIGS. 7A-16E are manufactured at a component level and then processed through surface preparation and attached to a guidewire, as further disclosed herein.

In one embodiment, as shown in FIGS. 7A-7E, a conically-shaped distal tip 30 has a generally conical surface 31. A recess 32 is formed in the distal end 33 of the conically-shaped distal tip 30 and is configured to provide an edge 34 that will hold the distal tip 30 in place when the recess engages hard plaque. At a proximal end 35 of the distal tip 30, a cavity 36 is formed which is configured for mounting on the distal end 24 of the distal core section 13 (see FIG. 3). The roughened surface 28 increases the frictional engagement of the distal tip with the hardened plaque with an increased likelihood that the distal tip will successfully advance through the plaque.

In another embodiment, as shown in FIGS. 8A-8E, a conically-shaped distal tip 40 has a generally conical surface 41. A slightly rounded nose cone 42 is formed in the distal end 43 of the conically-shaped distal tip 40 and is configured to provide an projection 44 that will hold the distal tip 40 in place when the projection 44 engages hard plaque. At a proximal end 45 of the distal tip 40, a cavity 46 is formed which is configured for mounting on the distal end 24 of the distal core section 13 (see FIG. 3). The roughened surface 28 increases the frictional engagement of the distal tip with the hardened plaque with an increased likelihood that the distal tip will successfully advance through the plaque.

In another embodiment, as shown in FIGS. 9A-9E, a frusto-conical-shaped distal tip 50 has a generally conical surface 51. A recess 52 is formed in the distal end 53 of the frusto-conical-shaped distal tip 50 and is configured to provide an edge 54 that will hold the distal tip 50 in place when the recess 52 engages hard plaque. At a proximal end 55 of the distal tip 50, a cavity 56 is formed which is configured for mounting on the distal end 24 of the distal core section 13 (see FIG. 3). The roughened surface 28 increases the frictional engagement of the distal tip with the hardened plaque with an increased likelihood that the distal tip will successfully advance through the plaque.

In another embodiment, as shown in FIGS. 10A-10E, a frusto-conical-shaped distal tip 60 has a generally conical surface 61. A recess 62 is formed in the distal end 63 of the frusto-conical-shaped distal tip 60 and is configured to provide an edge 64 that will hold the distal tip 60 in place when the recess 62 engages hard plaque. At a proximal end 65 of the distal tip 60, a stem 66 is formed which is configured for inserting into and mounting on the distal end 24 of the distal core section 13 by inserting into the helical coil 14 (see FIG. 3). The roughened surface 28 increases the frictional engagement of the distal tip with the hardened plaque with an increased likelihood that the distal tip will successfully advance through the plaque.

In another embodiment, as shown in FIGS. 11A-11E, a mushroom-shaped distal tip 70 has a generally conical surface 71. A rounded nose cone 72 is formed in the distal end 73 of the conically-shaped distal tip 70 and is configured to provide a projection 74 that will hold the distal tip 70 in place when the rounded nose cone 72 engages hard plaque. At a proximal end 75 of the distal tip 70, a stem 76 is formed which is configured for inserting into and mounting on the distal end 24 of the distal core section 13 by inserting into the helical coil 14 (see FIG. 3). The roughened surface 28 increases the frictional engagement of the distal tip with the hardened plaque with an increased likelihood that the distal tip will successfully advance through the plaque.

In another embodiment, as shown in FIGS. 12A-12E, a frusto-conical-shaped distal tip 80 has a generally conical surface 81. A recess 82 is formed in the distal end 83 of the frusto-conical-shaped distal tip 80 and is configured to provide an edge 84 that will hold the distal tip 80 in place when the recess 82 engages hard plaque. Multiple arcuate grooves 87 are formed into the conical surface 81 and are configured to bore into the hardened plaque like a drill bit when the physician twists or spins the guidewire. Thus, by twisting the guidewire and pushing simultaneously, the physician can advance the distal tip 80 and the arcuate grooves 87 into and through the plaque like a drill bit. At a proximal end 85 of the distal tip 80, a stem 86 is formed which is configured for inserting into and mounting on the distal end 24 of the distal core section 13 by inserting into the helical coil 14 (see FIG. 3). The roughened surface 28 increases the frictional engagement of the distal tip with the hardened plaque with an increased likelihood that the distal tip will successfully advance through the plaque.

In another embodiment, as shown in FIGS. 13A-13E, a partially conically-shaped distal tip 90 has a generally conical surface 91. A recess 92 is formed in the distal end 93 of the partially conically-shaped distal tip 90 and is configured to provide an edge 94 that will hold the distal tip 90 in place when the recess 92 engages hard plaque. At a proximal end 95 of the distal tip 90, a stem 96 is formed which is configured for inserting into and mounting on the distal end 24 of the distal core section 13 by inserting into the helical coil 14 (see FIG. 3). The roughened surface 28 increases the frictional engagement of the distal tip with the hardened plaque with an increased likelihood that the distal tip will successfully advance through the plaque.

In another embodiment, as shown in FIGS. 14A-14E, a partially conically-shaped distal tip 100 has a generally conical surface 101. A through hole 102 is formed in the distal end 103 of the partially conically-shaped distal tip 100 and is configured to provide an edge 104 that will hold the distal tip 100 in place when the edge 104 engages hard plaque. At a proximal end 105 of the distal tip 100, the through-hole 102 exits the distal tip 100 and is configured for mounting on the distal end 24 of the distal core section 13 (see FIG. 3). The roughened surface 28 increases the frictional engagement of the distal tip with the hardened plaque with an increased likelihood that the distal tip will successfully advance through the plaque.

In another embodiment, as shown in FIGS. 15A-15E, an angularly-shaped distal tip 110 has a partially conical surface 111. A recess 112 is formed in the distal end 113 of the angularly-shaped distal tip 110 and is configured to provide an edge 114 that will hold the distal tip 110 in place when the recess 112 engages hard plaque. The angularly-shaped distal tip 110 is angled because typically a physician puts a slight bend (with finger pressure) at the end of the helical coil 14 so that the guidewire can be advanced in a particular direction. In treating chronically stenosed lesions, a short angulation in the distal tip 110 is desired. This embodiment provides a short or small angulation to the distal tip 110 of the guidewire 10. At a proximal end 115 of the distal tip 110, a stem 116 is formed which is configured for inserting into and mounting on the distal end 24 of the distal core section 13 by inserting into the helical coil 14 (see FIG. 3). The roughened surface 28 increases the frictional engagement of the distal tip with the hardened plaque with an increased likelihood that the distal tip will successfully advance through the plaque.

In another embodiment, as shown in FIGS. 16A-16E, a partially conically-shaped distal tip 120 has a generally conical surface 121. A recess 122 is formed in the distal end 123 of the partially conically-shaped distal tip 120 and is configured to provide an edge 124 that will hold the distal tip 120 in place when the recess 122 engages hard plaque. At a proximal end 125 of the distal tip 120, a cavity 126 is formed which is configured for mounting on the distal end 24 of the distal core section 13 (see FIG. 3). The roughened surface 28 increases the frictional engagement of the distal tip with the hardened plaque with an increased likelihood that the distal tip will successfully advance through the plaque.

In all of the disclosed embodiments, the purpose and intent is to increase the surface roughness of the distal tip in order to enhance engagement with calcified and fibrous tissue (CTO). Several manufacturing methods have been developed to increase the surface roughness of the distal tip. In one method, once the distal tip has been soldered or otherwise attached to the guidewire distal end 24 or inserted into the helical coil 14, the distal tip is processed by micro bead blasting, laser roughening, sand paper, micro machining, and wire brushed to provide the desired level of surface roughness. Some of these manufacturing processes are easier to control than others, thus laser roughening is a preferred process because it is the most repeatable and manufacturing friendly version, providing the most options on texture type and degree of surface roughness.

In another manufacturing method, the distal tips can be manufactured at a component level and processed through surface preparation. These tips can then be attached to the core wire and coils via soldering/welding/adhesive or other suitable means. Tips can be manufactured by, but not limited to, stamping, casting, machining, micro molding, metal injection molding, and 3D printing and then further processed through surface treatments such as bead blasting, laser roughening, machining, sand paper, chemical etching, chemical vapor deposition or physical vapor deposition. FIGS. 7A-16E show some of the tip designs which can be machined, surface prepped and attached to the guide wire.

While reference has been made herein to the distal tip 20 being formed from a body solder 21, the distal tip 20 can be formed from other metal alloys or from plastics or polymers.

We claim:

1. A guidewire, comprising:
   an elongated core member having a proximal core section and a distal core section;
   a distal tip attached to a distal end of the distal core section, the distal tip formed from a metallic alloy or polymer and having a roughened outer surface for use in penetrating stenosed lesions in vessels; and
   the distal tip abuts a wire coil having an outer surface, wherein at least a distal portion of the outer surface of the wire coil has the same roughened outer surface as the distal tip.

2. The guidewire of claim 1, wherein the roughened surface is formed by physically altering the surface of the distal tip.

3. The guidewire of claim 2, wherein the physical alteration of the surface includes any of micro bead blasting, laser roughening, sand paper, micro machining, and wire brush.

4. The guidewire of claim 1, wherein an average surface roughness of the distal tip is in the range from 1 micron to 200 microns.

5. The guidewire of claim 1, wherein an average surface roughness of the distal tip is in the range from 1 micron to 10 microns.

6. The guidewire of claim 1, wherein an average surface roughness of the distal tip is in the range from 20 microns to 150 microns.

7. The guidewire of claim 1, wherein the distal tip is manufactured by any of stamping, casting, micro molding, machining, metal injection molding, and 3D printing.

8. The guidewire of claim 1, wherein the roughened surface of the distal tip is formed by any of chemical etching, chemical vapor deposition, and physical vapor deposition.

9. The guidewire of claim 1, wherein the distal tip has a structural configuration including any of rounded half-dome, conical, frusto-conical, mushroom-shaped, conical with a flattened tip, and conical with recessed tip.

10. A method of manufacturing a distal tip for attaching to a guidewire, comprising:
    forming a metal alloy or polymer into a distal tip;
    roughening an outer surface of the distal tip for use in penetrating stenosed lesions in a vessel; and
    wherein the distal tip abuts a wire coil having an outer surface, and simultaneously roughening at least a portion of the wire coil outer surface and the distal tip outer surface.

11. The method of claim 10, wherein an average surface roughness of the distal tip is in the range from 1 micron to 200 microns.

12. The method of claim 10, wherein an average surface roughness of the distal tip is in the range from 1 micron to 10 microns.

13. The method of claim 10, wherein an average surface roughness of the distal tip is in the range from 20 microns to 150 microns.

14. The method of claim 10, wherein roughening the surface of the distal tip includes any of micro bead blasting, laser roughening, applying sand paper, micro machining, and wire brushing.

15. The method of claim 10, wherein the distal tip is formed by any of stamping, casting, micro molding, machining, metal injection molding and 3D printing.

16. The method of claim 10, wherein roughening the surface of the distal tip includes any of chemical etching, chemical vapor deposition, and physical vapor deposition.

* * * * *